United States Patent [19]

Turner et al.

[11] Patent Number: 4,786,627
[45] Date of Patent: Nov. 22, 1988

[54] THIADIAZOLE GUANIDINES

[75] Inventors: Stephen Turner, Letchworth; Malcolm Myers, Hull, both of United Kingdom

[73] Assignee: Reckitt & Colman Products Limited, London, England

[21] Appl. No.: 179,298

[22] Filed: Apr. 8, 1988

[30] Foreign Application Priority Data

Apr. 24, 1987 [GB] United Kingdom ............... 8709734

[51] Int. Cl.$^4$ .................... C07D 285/12; A61K 31/41
[52] U.S. Cl. ..................................... 514/363; 548/138
[58] Field of Search ......................... 514/363; 548/138

[56] References Cited

U.S. PATENT DOCUMENTS 4,147,794  4/1979  Turner ................................. 514/363

OTHER PUBLICATIONS

J. Med. Chem, 1987, 30, 951.
J. Med. Chem, 1986, 29, 2273.
J. Med. Chem., 1986, 29, 2280.

Primary Examiner—Robert Gerstl
Attorney, Agent, or Firm—Bacon & Thomas

[57] ABSTRACT

Thiadiazole guanidines of formula 1

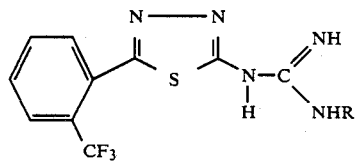

wherein R is hydrogen or $C_{1-4}$ alkyl and their non-toxic salts.

Processes for their preparation and pharmaceutical compositions thereof. The compounds exhibit anti-convulsant activity and are indicated for use in the treatment of epilepsy.

9 Claims, No Drawings

THIADIAZOLE GUANIDINES

This invention relates to thiadiazole guanidines, their non-toxic salts, processes for their preparation and pharmaceutical compositions of the derivatives or their salts.

According to this invention there are provided compounds of the formula:

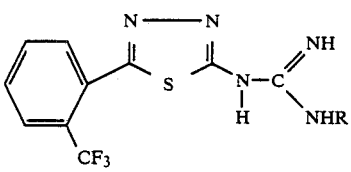

wherein R is hydrogen or alkyl $C_{1-4}$ and their non-toxic salts.

In a preferred aspect in the compounds of formula 1 R is hydrogen or methyl.

The invention also includes pharmaceutical compositions comprising a compound of formula 1 or a non-toxic salt thereof together with a pharmaceutically acceptable diluent or carrier.

Examples of non-toxic salts are those with inorganic acids such as hydrochloric acid, sulphuric acid or phosphoric acid or organic acids such as acetic, propionic, malonic, succinic, fumaric, tartaric, citric or cinnamic acid.

The compounds of formula 1 have been shown in animal tests to exhibit potent anticonvulsant activity.

The invention also includes a method of treating epilepsy which comprises administering to a patient suffering from epilepsy an effective amount of a compound of formula 1 or a non-toxic salt thereof.

The compound of formula 1 in which R is hydrogen may be prepared from a compound of formula 2

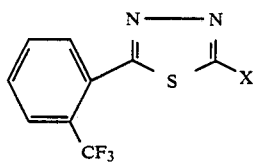

in which X is chloro or bromo by reaction with guanidine. Conveniently the reaction is carried out using an excess (3-5 molar equivalents) of guanidine at a temperature in the range 60°-140° C. in an anhydrous polar solvent such as t-butanol or dioxan.

The compounds of formula 1 in which R is alkyl $C_{1-4}$ may be prepared from a compound of formula 2 in which X is chloro or bromo by reaction with sodium cyanamide followed by reaction of the resultant substituted cyanamide with an amine $RNH_2$ where R is alkyl $C_{1-4}$.

Conveniently the reaction of the compound of formula 2 with sodium cyanamide is carried out in an anhydrous polar solvent such as dimethylformamide. Reaction of the resultant substituted cyanamide with the amine $RNH_2$ is conveniently carried out at a temperature in the range 60°-140° C.

The invention is illustrated by the following Examples. Melting points were determined on a Kofler hot stage apparatus or a Buchi apparatus in glass capillary tubes and are uncorrected.

EXAMPLE 1

2-Guanidino-5-[2-(trifluoromethyl)phenyl]-1,3,4-thiadiazole hydrochloride

A stirred mixture of sodium (4.34 g, 189 mmol) and anhydrous t-BuOH (250 mL) was heated at 80°-90° C. under an atmosphere of nitrogen until the metal had dissolved. After cooling, guanidine hydrochloride (20.24 g, 213 mmol) was added with stirring. After 0.5 h a solution of 2-chloro-5-[2-(trifluoromethyl)phenyl]-1,3,4-thiadiazole (16.5 g, 62.4 mmol) in t-BuOH (25 mL) was added and heating at 80°-90° C. was continued for a further 24 h. Solvent was removed in vacuo and the residue was stirred with water (550 mL). The resultant solid was collected, washed with water and dried to afford the free base (15.94 g) which was converted to its hydrochloride salt using EtOH and ethereal HCl. Crystallisation from $MeOH.Et_2O$ gave the desired product: yield 13.2 g (65%); mp 164°-165° C.

EXAMPLE 2

2-(3-Methylguanidino)-5-[2-(trifluoromethyl)phenyl]-1,3,4-thiadiazole (a)

2-Cyanamido-5-[2-(trifluoromethyl)phenyl]-1,3,4-thiadiazole

A stirred mixture of sodium cyanamide (0.16 g, 2.5 mmol) and anhydrous DMF (3 mL) under a nitrogen atmosphere was treated with solution of 2-chloro-5-[2-(trifluoromethyl)phenyl]-1,3,4-thiadiazole (0.27 g, 1 mmol) in anhydrous DMF (2 mL). The mixture was stirred for 16 h at room temperature. Solvent was removed in vacuo and the residue was stirred with water (10 mL) during the addition of aqueous 2N HCl until the pH was 2. Extraction with $Et_2O$ followed by drying of the extracts and evaporation gave the desired cyanamide: yield 0.22 g (82%); MS 270 ($M^+$)($C_{10}H_5F_3N_4S$ requires $M^+$ 270). The product was used directly without further purification.

(b)

2-(3-Methylguanidino)-5-[2-(trifluoromethyl)phenyl]-1,3,4-thiadiazole

A solution of the above cyanamide (3 g, 11.1 mmol) in methylamine (42 mL of 40% aqueous solution) was heated for 16 h at 110° C. in a sealed tube. On cooling, the contents were stirred with $Et_2O$ (450 mL) to dissolve most of the solid that had precipitated. Any undissolved solid was removed by filtration. The organic layer was evaporated to dryness to leave 1.7 g of a solid which was purified by chromatography on grade III alumina eluting with $CHCl_3$ to give the desired product: yield 1.02 g (30%); mp 160°-162° C.

EXAMPLE 3

2-(3-n-Butylguanidino)-5-[2-(trifluoromethyl)phenyl]-1,3,4-thiadiazole hydrochloride This was prepared by heating the cyanamido compound of Example 2(a) with butylamine under reflux conditions (110°-120° C. bath temperature). The product obtained as the hydrochloride after recrystallisation from acetone had mp 147°-149° C.

The pharmacological activity of the compounds of the invention have been determined according to the following procedures. Their anticonvulsant activity was determined in the metrazol antagonism test in mice (MMS) (Soaje-Echaque E; Lim RKS, *J Pharmac Exp Ther* 1962, 138, 224; Desmedt LKC; Niemegeers CJE; Lewi PJ; Janssen PAJ, *Arzneim-Forsch* (Drug Res), 1976, 26, 1592) and the electroshock test in mice (MES)- (Tulloch IF; Walter DS; Howe GM; Howe SJ, *Neuropharmacology* 1982, 21, 555).

Table 1 shows the effects of the compounds of Examples 1 and 2 on maximal electroshock seizures (MES) in the rat and maximal metrazol seizures (MMS) in the mouse and rat compared with three established anticonvulsant drugs after oral administration at t=1 hour.

TABLE 1

| COMPOUND | Inhibition of Hind Limb Tonus $ED_{50}$ mg/Kg (limits) | | |
|---|---|---|---|
| | RAT | MOUSE | |
| | MES | MES | MMS |
| Example 1 | 22(11–34) | 27(17–43) | 45(17–70) |
| Example 2 | ND | 49(32–65) | 44(31–82) |
| phenytoin | 14(6–23) | 8(4–12) | 8(6–11) |
| phenobarbital | 9(7–13) | 12(9–15) | 4(3–6) |
| carbamazepine | 4(2–7) | 20(17–23) | 11(2–16) |

From the Table it can be seen that in the rat and the mouse the compounds of Examples 1 and 2 were potent anticonvulsants blocking both electrically and chemically induced seizures.

An assessment of the neurotoxicity of the compounds of Examples 1 and 2 was carried out in mice using the rotorod test (Collier HOJ; Fieller EC; Hall RA, *Analyst*, 1949, 74, 592). The data in Table 2 shows $TD_{50}$ values at the time of peak anticonvulsant effect obtained with the compounds and the standard drugs after oral administration in the mouse.

TABLE 2

| COMPOUND | $TD_{50}$ mg/Kg[a] At 1 hour |
|---|---|
| Example 1 | 324(171–INF)[b] |
| Example 2 | >400(INF) |
| Phenytoin | 216(154–319) |
| Phenobarbital | 68(52–92) |
| Carbamazepine | 166(104–282) |

[a]Dose at which 50% of trained animals fall off the rotorod
[b]95% Confidence limits From the Table it can be seen that in the compounds of Examples 1 and 2 the level of neurotoxicity was at an acceptable level.

The pharmaceutical compositions may be in a form suitable for oral, rectal or parenteral administration. Such oral compositions may be in the form of capsules, tablets, granules or liquid preparations such as elixirs, syrups or suspensions.

Tablets contain a compound of formula 1 or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or kaolin in a hard gelatine capsule.

Compositions for parental administration may be in the form of sterile injectable preparations such as solutions or suspensions in for example water, saline or 1,3-butane diol.

For the purpose of convenience and accuracy of dosing the compositions are advantageously employed in a unit dosage form. For oral administration the unit dosage form contains from 1 to 200 mg, preferably 5 to 100 mg of the compound of formula 1 or a non-toxic salt thereof. Parenteral unit dosage forms contain from 0.1 to 25 mg of the compound of formula 1 or a non-toxic salt thereof per 1 ml of the preparation.

The invention is further illustrated by the following Examples of compositions in which are parts are by weight.

EXAMPLE I

A mixture of one part 2-guanidino-5-[2-(trifluoromethyl)phenyl]-1,3,4-thiadiazole hydrochloride and four parts microcrystalline cellulose together with 1% of magnesium stearate is compressed into tablets. Conveniently the tablets are of such size to contain 5, 10, 25, 50 or 100 mg of the active ingredient.

EXAMPLE II

A mixture of one part 2-guanidino-5-[2-(trifluoromethyl)phenyl]-1,3,4-thiadiazole hydrochloride and four parts spray dried lactose together with 1% magnesium stearate is filled into hard gelatine capsules. The capsules may conveniently contain 5, 10, 25, 50 or 100 mg of the active ingredient.

We claim:
1. A compound of the formula

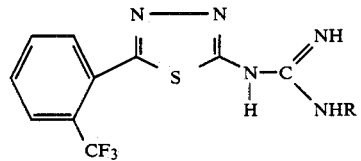

wherein R is hydrogen or alkyl $C_{1-4}$ and its non-toxic salts.

2. A compound of the formula 1 of claim 1 wherein R is hydrogen or methyl and its non-toxic salts.

3. 2-Guanidino-5-[2-(trifluoromethyl)phenyl]-1,3,4-thiadiazole.

4. 2-(3-Methylguanidino)-5-[2-(trifluoromethyl)phenyl]-1,3,4-thiadiazole.

5. A pharmaceutical composition for the treatment of epilepsy which comprises an effective amount of at least one compound as claimed in claim 1 or a non-toxic salt thereof together with a pharmaceutically acceptable diluent or carrier.

6. A pharmaceutical composition as claimed in claim 5 in unit dosage form for oral administration comprising from 1 to 200 mg of the compound or a non-toxic salt thereof per unit dosage.

7. A pharmaceutical composition as claimed in claim 5 in unit dosage form for oral administration comprising from 5 to 100 mg of the compound or a non-toxic salt thereof.

8. A pharmaceutical composition as claimed in claim 5 in unit dosage form for parenteral administration comprising from 0.1 to 25 mg of the compound or a non-toxic salt thereof per 1 mL of the composition.

9. A method of treating epilepsy which comprises administering to a patient suffering from epilepsy an effective amount of a compound claimed in claim 1 or a non-toxic salt thereof.

* * * * *